(12) United States Patent
Fan et al.

(10) Patent No.: US 11,753,743 B2
(45) Date of Patent: Sep. 12, 2023

(54) HIGH-THROUGHPUT SINGLE-CELL POLYOMICS

(71) Applicant: Yale University, New Haven, CT (US)

(72) Inventors: Rong Fan, Cheshire, CT (US); Burak Dura, Waltham, CO (US)

(73) Assignee: Yale University, New Haven, CT (US)

( * ) Notice: Subject to any disclaimer, the term of this patent is extended or adjusted under 35 U.S.C. 154(b) by 881 days.

(21) Appl. No.: 16/485,326

(22) PCT Filed: Feb. 13, 2018

(86) PCT No.: PCT/US2018/017900
§ 371 (c)(1),
(2) Date: Aug. 12, 2019

(87) PCT Pub. No.: WO2018/148700
PCT Pub. Date: Aug. 16, 2018

(65) Prior Publication Data
US 2019/0360121 A1 Nov. 28, 2019

Related U.S. Application Data

(60) Provisional application No. 62/458,283, filed on Feb. 13, 2017.

(51) Int. Cl.
| | | |
|---|---|---|
| C40B 20/04 | (2006.01) |
| C12N 15/10 | (2006.01) |
| C40B 70/00 | (2006.01) |
| C40B 20/02 | (2006.01) |

(52) U.S. Cl.
CPC .......... *C40B 20/04* (2013.01); *C12N 15/1065* (2013.01); *C40B 20/02* (2013.01); *C40B 70/00* (2013.01); *B01J 2219/00317* (2013.01); *B01J 2219/00547* (2013.01); *B01J 2219/00572* (2013.01); *B01J 2219/00659* (2013.01); *C12Q 2563/179* (2013.01); *C12Q 2565/514* (2013.01)

(58) Field of Classification Search
CPC ................. C12N 15/1065; C40B 70/00; B01J 2219/00317; B01J 2219/00547; B01J 2219/00659; C12Q 2563/179
See application file for complete search history.

(56) References Cited

U.S. PATENT DOCUMENTS

| | | |
|---|---|---|
| 9,188,586 B2 | 11/2015 | Fan et al. |
| 9,506,917 B2 | 11/2016 | Fan et al. |
| 10,274,486 B2 | 4/2019 | Fan et al. |
| 10,928,389 B2 | 2/2021 | Fan et al. |
| 2008/0268451 A1 | 10/2008 | Seligmann et al. |
| 2009/0137413 A1 | 5/2009 | Mehta et al. |
| 2015/0204864 A1 | 7/2015 | Fan et al. |
| 2015/0298091 A1 | 10/2015 | Weitz et al. |
| 2016/0054308 A1 | 2/2016 | Guo |
| 2016/0251714 A1 | 9/2016 | Conant et al. |
| 2019/0276880 A1 | 9/2019 | Fan et al. |
| 2021/0095331 A1 | 4/2021 | Fan et al. |
| 2022/0057388 A1 | 2/2022 | Fan et al. |

FOREIGN PATENT DOCUMENTS

| | | | |
|---|---|---|---|
| WO | WO 2007/035633 A2 | 3/2007 | |
| WO | WO 2014/031997 A1 | 2/2014 | |
| WO | WO-2014031997 A1 * | 2/2014 | ....... G01N 33/54306 |
| WO | WO 2014/200767 A1 | 12/2014 | |
| WO | WO 2015/044428 A1 | 4/2015 | |
| WO | WO 2016/090148 A1 | 6/2016 | |
| WO | WO-2016138496 A1 * | 9/2016 | ........... C12Q 1/6813 |
| WO | WO 2016/168825 A1 | 10/2016 | |
| WO | WO 2017/087873 A1 | 5/2017 | |
| WO | WO-2017087873 A1 * | 5/2017 | ............ B01L 3/5025 |
| WO | WO 2018/017469 A1 | 1/2018 | |
| WO | WO 2018/064640 A1 | 4/2018 | |
| WO | WO 2021/067246 A1 | 4/2021 | |

OTHER PUBLICATIONS

Fan, Rong, et al. "Integrated barcode chips for rapid, multiplexed analysis of proteins in microliter quantities of blood." Nature biotechnology 26.12 (2008): 1373-1378. (Year: 2008).*
Fan, Rong, et al. Nature biotechnology 26.12 (2008): 1373-1378; supplementary information (Year: 2008).*
PCT/US2018/017900, May 25, 2018, International Search Report and Written Opinion.
PCT/US2018/017900, Aug. 22, 2019, International Preliminary Report on Patentability.
Extended European Search Report for EP Application No. 18751490.6 dated Mar. 2, 2021.
Kivioja et al., Counting absolute numbers of molecules using unique molecular identifiers. Nat Methods. Nov. 20, 2011;9(1):72-4. doi: 10.1038/nmeth.1778.
EP 18751490.6, Mar. 2, 2021, Extended European Search Report.
Agasti et al., Photocleavable DNA barcode-antibody conjugates allow sensitive and multiplexed protein analysis in single cells. J Am Chem Soc. Nov. 14, 2012;134(45):18499-502. doi: 10.1021/ja307689w. Epub Nov. 2, 2012.
Chen et al., Single-Cell Protein Secretion Detection and Profiling. Annu Rev Anal Chem (Palo Alto Calif). Jun. 12, 2019;12(1):431-449. doi: 10.1146/annurev-anchem-061318-115055. Epub Apr. 12, 2019.
Delley et al., Combined aptamer and transcriptome sequencing of single cells. Sci Rep. Feb. 13, 2018;8(1):2919.
Deng et al., An integrated microfluidic chip system for single-cell secretion profiling of rare circulating tumor cells. Sci Rep. Dec. 16, 2014;4:7499.

(Continued)

*Primary Examiner* — Sahana S Kaup
(74) *Attorney, Agent, or Firm* — Wolf, Greenfield & Sacks, P.C.

(57) ABSTRACT

Provided herein, in some embodiments, are devices, systems and methods for high-throughput single-cell polyomics (e.g., genomic, epigenomic, proteomic and/or phenotypic profile) analyses.

17 Claims, 9 Drawing Sheets

Specification includes a Sequence Listing.

(56) References Cited

OTHER PUBLICATIONS

Deng et al., Single-Cell Omics Analyses Enabled by Microchip Technologies. Annu Rev Biomed Eng. Jun. 4, 2019;21:365-393. doi: 10.1146/annurev-bioeng-060418-052538. Epub Mar. 18, 2019.
Fan et al., Integrated blood barcode chips. Nat Biotechnol. Dec. 2008;26(12):1373-8. doi: 10.1038/nbt.1507. Epub Nov. 16, 2008.
Gong et al., Simple method to prepare oligonucleotide-conjugated antibodies and its application in multiplex protein detection in single cells. Bioconjug Chem. Jan. 20, 2016;27(1):217-25. doi: 10.1021/acs.bioconjchem.5b00613. Epub Jan. 4, 2016.
Liu et al., High-Spatial-Resolution Multi-Omics Sequencing via Deterministic Barcoding in Tissue. Cell. Dec. 10, 2020;183(6):1665-1681.e18. doi: 10.1016/j.cell.2020.10.026. Epub Nov. 13, 2020.
Maïno et al., A microfluidic platform towards automated multiplexed in situ sequencing. Sci Rep. Mar. 5, 2019;9(1):3542.
Wei et al., Microchip platforms for multiplex single-cell functional proteomics with applications to immunology and cancer research. Genome Med. 2013; 5(75): 1-12.

\* cited by examiner

FIG. 3

Step 1 - immobilize T7 promoter and sequencing adapter sequences with row barcodes (Barcodes A) to glass slide

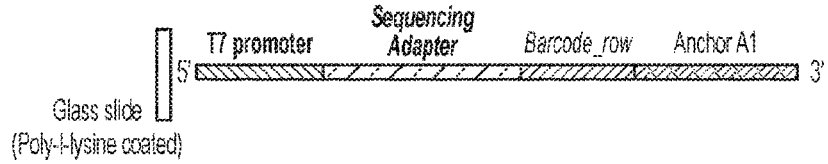

Step 2 - Hybridize the column barcodes (Barcodes B)

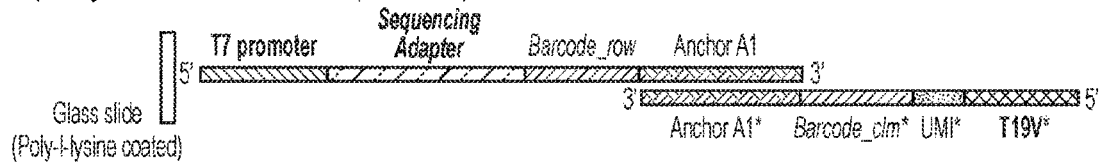

Step 3 - Extend the column barcodes (primer extension reaction)

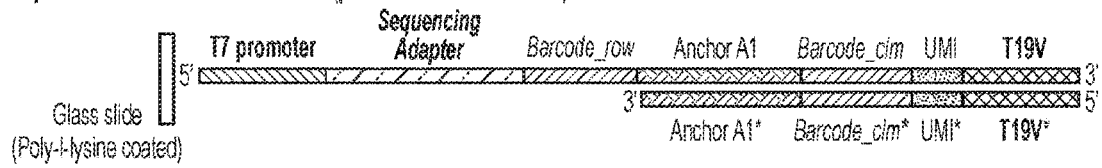

Step 4 - Strip off the second strands to finalize molecular barcodes terminated with poly(dT) sequence for mRNA capture

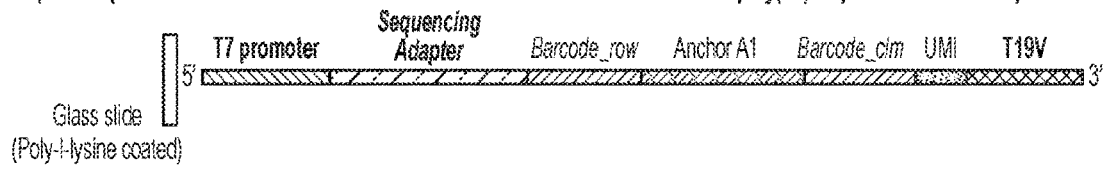

FIG. 4

Patterning of column barcodes (Barcodes A)

Extension of row barcodes (Barcodes B)

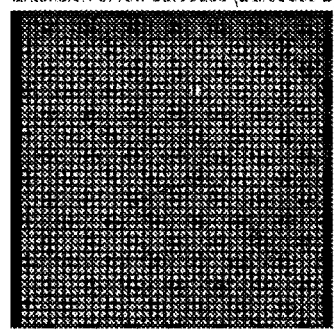

Row barcode 20

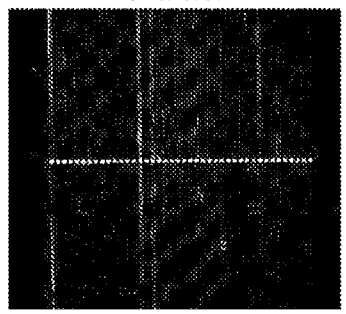

Column barcode 19

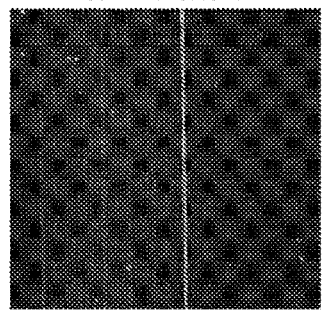

FIG. 13
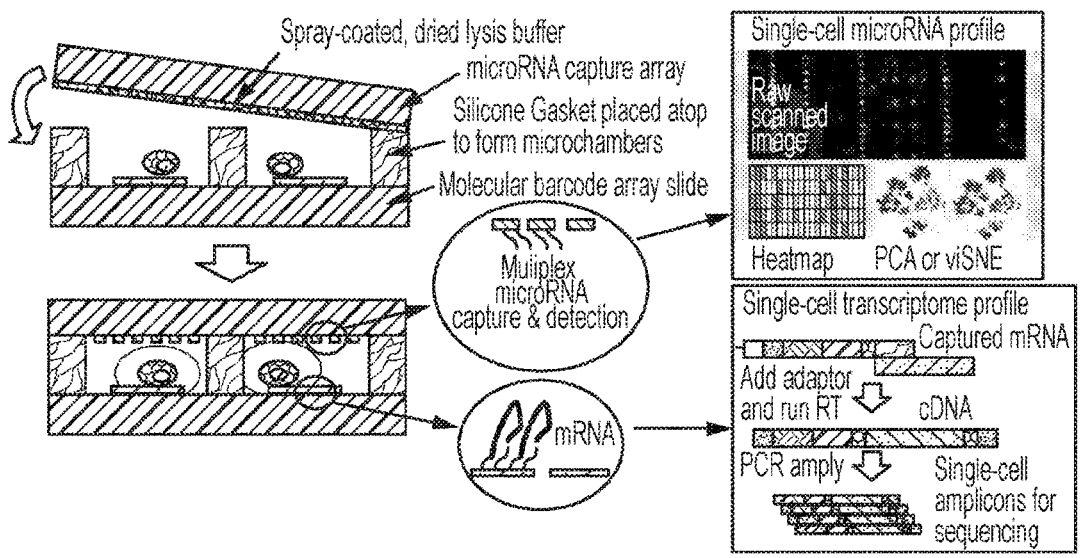
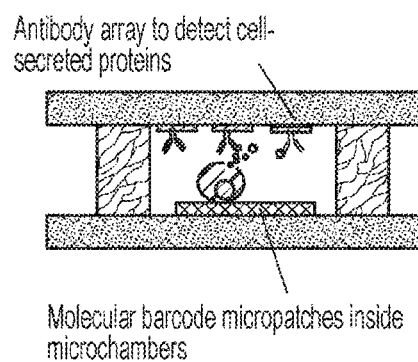
FIG. 14A
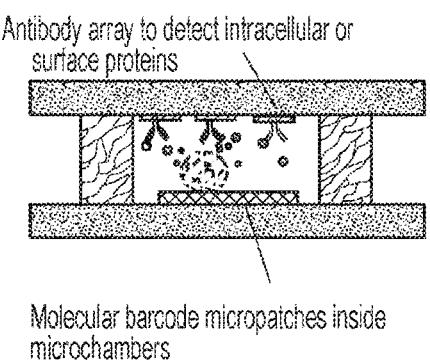
FIG. 14B

SEQUENCE LISTING

<160> NUMBER OF SEQ ID NOS: 16

<210> SEQ ID NO 1
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 1
cgattgagcc ggttttttta agcagtggta tcaacgcaga gtacagtaca tcgagtgatt    60
gcttgtgacg                                                           70

<210> SEQ ID NO 2
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 2
cgattgagcc ggttttttta agcagtggta tcaacgcaga gtaccacgtc agtgagtgat    60
tgcttgtgac g                                                         71

<210> SEQ ID NO 3
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 3
cgattgagcc ggttttttta agcagtggta tcaacgcaga gtacgtacgt gagcgagtga    60
ttgcttgtga cg                                                        72

<210> SEQ ID NO 4
<211> LENGTH: 73
<212> TYPE: DNA
<213> ORGANISM: Artificial Sequence
<220> FEATURE:
<223> OTHER INFORMATION: Synthetic polynucleotide

<400> SEQUENCE: 4
cgattgagcc ggttttttta agcagtggta tcaacgcaga gtactcgtag ctcgtgagtg    60
attgcttgtg acg                                                       73

<210> SEQ ID NO 5
<211> LENGTH: 72
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(38)
<223> OTHER INFORMATION: n is a, c, g, or t

<400> SEQUENCE: 5
aaaaaaaaaa aaaaaaaaaa aaaaaaaaaa nnnnnnnnta cgagctgtca tcagcgtcac    60
aagcaatcac tc                                                        72

<210> SEQ ID NO 6
<211> LENGTH: 72
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(38)
<223> OTHER INFORMATION: n is a, c, g, or t

<400> SEQUENCE: 6
aaaaaaaaaa aaaaaaaaaa aaaaaaaaaa nnnnnnnncg actcaggtca tcagcgtcac    60
aagcaatcac tc                                                        72

<210> SEQ ID NO 7
<211> LENGTH: 72
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(38)
<223> OTHER INFORMATION: n is a, c, g, or t

<400> SEQUENCE: 7
aaaaaaaaaa aaaaaaaaaa aaaaaaaaaa nnnnnnnnat gtgagcgtca tcagcgtcac    60
aagcaatcac tc                                                        72

<210> SEQ ID NO 8
<211> LENGTH: 72
<212> TYPE: DNA
<213> ORGANISM: Artificial Sequence
<220> FEATURE:

```
<223> OTHER INFORMATION: Synthetic polynucleotide
<220> FEATURE:
<221> NAME/KEY: misc_feature
<222> LOCATION: (31)..(38)
<223> OTHER INFORMATION: n is a, c, g, or t

<400> SEQUENCE: 8
aaaaaaaaaa aaaaaaaaaa aaaaaaaaaa nnnnnnnngc gacatagtca tcagcgtcac    60
aagcaatcac tc                                                        72

<210> SEQ ID NO 9
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 9
gtacgtgagc                                                           10

<210> SEQ ID NO 10
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 10
tcgtagctcg t                                                         11

<210> SEQ ID NO 11
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 11
gctcacgtac                                                           10

<210> SEQ ID NO 12
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 12
acgagctacg a                                                         11

<210> SEQ ID NO 13
<211> LENGTH: 124
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (87)..(94)
<223> OTHER INFORMATION: n is a, c, g, or t

<400> SEQUENCE: 13
cgattgagcc ggttttttta agcagtggta tcaacgcaga gtacagtaca tcgagtgatt    60
gcttgtgacg ctgatgacag ctcgtannnn nnnntttttt tttttttttt tttttttttt   120
tttt                                                                124
```

```
<210> SEQ ID NO 14
<211> LENGTH: 125
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (88)..(95)
<223> OTHER INFORMATION: n is a, c, g, or t

<400> SEQUENCE: 14
cgattgagcc ggttttttta agcagtggta tcaacgcaga gtaccacgtc agtgagtgat        60
tgcttgtgac gctgatgacc tgagtcgnnn nnnnntttt tttttttttt tttttttttt       120
ttttt                                                                  125

<210> SEQ ID NO 15
<211> LENGTH: 126
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (89)..(96)
<223> OTHER INFORMATION: n is a, c, g, or t

<400> SEQUENCE: 15
cgattgagcc ggttttttta agcagtggta tcaacgcaga gtacgtacgt gagcgagtga        60
ttgcttgtga cgctgatgac gctcacatnn nnnnnntttt tttttttttt tttttttttt       120
tttttt                                                                 126

<210> SEQ ID NO 16
<211> LENGTH: 127
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (90)..(97)
<223> OTHER INFORMATION: n is a, c, g, or t

<400> SEQUENCE: 16
cgattgagcc ggttttttta agcagtggta tcaacgcaga gtactcgtag ctcgtgagtg        60
attgcttgtg acgctgatga ctatgtcgcn nnnnnnnttt tttttttttt tttttttttt       120
ttttttt                                                                127
```

HIGH-THROUGHPUT SINGLE-CELL POLYOMICS

RELATED APPLICATION

This application is a national stage filing under 35 U.S.C. § 371 of international application number PCT/US2018/017900, filed Feb. 13, 2018, which was published under PCT Article 21(2) in English and claims the benefit under 35 U.S.C. § 119(e) of U.S. provisional application No. 62/458,283, filed Feb. 13, 2017, which is incorporated by reference herein in its entirety.

SUMMARY

Provided herein, in some embodiments, are devices, systems and methods for high-throughput single-cell polyomics (e.g., genomic, epigenomic, proteomic and/or phenotypic profile) analyses. The technology as provided herein may be used, for example, to process in parallel tens of thousands of single cells using deterministic molecular barcodes in a spatially-defined array. With this technology, multiple "omics" (polyomic) information can be linked to the same cell (or subpopulation of cells) based on the spatial location of the cell and the corresponding molecular barcode(s). More than 400,000 single cells can be processes in parallel in one microfluidic unit, for example. This throughput is higher than (e.g., 5-10× higher than) current sequencing and genomic technologies.

Deterministic barcoding is used to assign each cell a predetermined molecular (e.g., nucleic acid and/or protein) barcode sequence, which is associated with a predetermined location such that multiple measurements on the same cell (or subpopulation of cells) can be linked together through the barcode and location.

This technology enables the acquisition of the entire repertoire of information in cells of a biological system (including low cell number/low quality samples), enabling unprecedented access to the multimodal layers of molecular regulation that underlie biological complexity, and can be used to unveil the mechanisms that underlie such complexity (e.g., how epigenetic alterations regulate transcriptional expression and/or protein signaling).

The devices, systems and methods of the present disclosure are ideal for use in the clinical setting, for example. This technology can be used with low quality samples (e.g., including low cell numbers), reduces sequencing cost per cell, and improves resolution for distinguishing rare cell subsets and detecting rare disease-causing cells (e.g., pathogenic cells).

Thus, some aspects of the present disclosure provide a polyomic multiplexing device, comprising a substrate comprising X columns intersecting Y rows to form X*Y patches, wherein each of the X*Y patches comprises a unique nucleic acid barcode that is immobilized to the substrate and comprises a polyT sequence, wherein each column comprises a different subset of barcoded nucleic acid strands of a first set of nucleic acid strands, and each row comprises a different subset of barcoded nucleic acid strands of a second set of nucleic acid strands, and wherein the nucleic acid strands of the first set are bound to nucleic acid strands of the second set to form a unique nucleic acid barcode. See, e.g., FIG. 15D.

In some embodiments, X is at least 10. Thus, in some embodiments, the device comprises at least 10 columns. In some embodiments, X is at least 20, at least 50, at least 100, at least 1000, at least 10000, or at least 20000. In some embodiments, X is 10 to 20000.

In some embodiments, Y is at least 10. Thus, in some embodiments, the device comprises at least 10 rows. In some embodiments, Y is at least 20, at least 50, at least 100, at least 1000, at least 10000, or at least 20000. In some embodiments, Y is 10 to 20000.

In some embodiments, the device further comprises $Z_{n+1}$ columns intersecting the Y rows to form Y*Z patches, wherein each of the Y*Z patches comprises a molecular binding partner (e.g., antibody) immobilized to the substrate, and wherein n is zero or greater (e.g., n is 1, 2, 3, 4, or 5). In some embodiments, n is at least 1, and each of the $Z_{n+1}$ columns comprises a different molecular binding partner (e.g., a different antibody, e.g., antibody A, antibody B, etc.). In some embodiments, n is at least 2, and each of the $Z_{n+1}$ columns comprises a different molecular binding partner (e.g., a different antibody, e.g., antibody A, antibody B, antibody C, etc.). In some embodiments, the molecular binding partner is an antibody. The term "antibody" includes whole antibodies and antibody fragments (e.g., scFv and/or Fab fragments).

In some embodiments, the device further comprises an array of microwells coupled to the substrate (e.g., such that each microwell formed a seal with the substrate), wherein each microwell comprises one of the unique molecular barcodes of the substrate. See, e.g., FIG. 15D. In some embodiments, the device further comprises an array of microwells coupled to the substrate, wherein each microwell comprises one of the unique molecular barcodes of the substrate and at least one of the molecular binding partners. Thus, each microwell may be encoded by a molecular signature that includes a unique combination of nucleic acids and antibodies.

It should be understood that the term "unique" is with respect to the components of a single device and means "only one" of a particular component (or subset of components) of the device. Thus, a patch comprising a unique nucleic acid barcode (or a unique subset of nucleic acid barcodes) is the only patch on the device that includes that particular unique nucleic acid barcode (or unique subset of nucleic acid barcodes), such that the patch (and any microwell associated with the patch and any cell(s) within that microwell) can be identified based on that unique nucleic acid barcode (or a unique subset of nucleic acid barcodes).

In some embodiments, the microwell array (and thus the device) comprises at least 20 microwells. For example, the microwell array may comprise at least 50, at least 100, at least 1000, or at least 10000 microwells. In some embodiments, the microwell array comprises 10, 20, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, or 40000 microwells.

In some embodiments, the nucleic acid strands of the first set of nucleic acid strands comprise, optionally in the 5' to 3' direction: a promoter sequence (e.g., a T7 promoter sequence), a sequencing adaptor sequence, a first barcode sequence (e.g., unique to the first set of nucleic acid strands and/or unique to subsets of nucleic acid strands within the first set) and a first anchor sequence. In some embodiments, the nucleic acid strands of the second set of nucleic acid strands comprise, optionally in the 5' to 3' direction: a polyT sequence, a unique molecular identifier sequence, a second barcode sequence (e.g., unique to the second set of nucleic acid strands and/or unique to subsets of nucleic acid strands within the second set) and a second anchor sequence, wherein the second anchor sequence is complementary to the first anchor sequence. In some embodiments, the unique nucleic acid barcode comprises, optionally in the 5' to 3' direction: a promoter sequence, a sequencing adaptor sequence, a first barcode sequence, a second barcode sequence, optionally a unique molecular identifier, and a polyT sequence.

In some embodiments, the substrate comprises glass, silicon or silica. In some embodiments, the substrate is coated with poly-1-lysine.

In some embodiments, the each column and/or row has a width of 50-200 microns. In some embodiments, each column and/or row has a width of 100 microns.

In some embodiments, each patch has an area of 400-40,000 $\mu m^2$. In some embodiments, each patch has an area of 10,000 $\mu m^2$.

In some embodiments, the patches within a single row and/or within a single column are separated from each other by 20-200 microns. In some embodiments, the patches within a single row and/or within a single column are separated from each other by 100 microns.

In some embodiments, the patches between adjacent rows and/or between adjacent columns are separated from each other by 20-200 microns. In some embodiments, the patches between adjacent rows and/or between adjacent columns are separated from each other by 100 microns.

Some aspects of the present disclosure provide a polyomic multiplexing device, comprising a microwell array comprising at least 20 microwells, wherein each microwell of the array comprises a molecular barcode specific to a single microwell, and wherein each molecular barcode comprises (a) a nucleic acid barcode that comprises a polyT sequence and (b) at least one antibody. In some embodiments, the device comprises at least 2, at least 3, or at least 4 different antibodies. In some embodiments, the microwell (and thus the device) comprises at least 50, at least 100, at least 1000, or at least 10000 microwells. In some embodiments, the unique nucleic acid barcode comprises, optionally in the 5' to 3' direction: a promoter sequence, a sequencing adaptor sequence, a first barcode sequence, a second barcode sequence, optionally a unique molecular identifier, and the polyT sequence.

Other aspects of the present disclosure provide a method of producing a barcoded array, comprising (a) flow patterning and immobilizing onto a surface of a substrate a first set of barcoded nucleic acid strands of a first solution to produce columns that are parallel to and space apart relative to each other, wherein each column comprises X patches of barcoded nucleic acid strands of the first set, wherein the patches within each column are spaced apart relative to each other, wherein each column comprises a different subset of barcoded nucleic acid strands, and wherein X is a number greater than 2; (b) flow patterning and immobilizing onto the surface of the substrate a second set of barcoded nucleic acid strands of a second solution to produce rows that are parallel to and space apart relative to each other, wherein each row comprises Y patches of barcoded nucleic acid strands of the second set, wherein the patches within each row are spaced apart relative to each other, wherein each row comprises a different subset of barcoded nucleic acid strands, wherein the rows are perpendicular relative to the columns, and wherein Y is a number greater than 2, thereby producing a X*Y array of patches, each patch comprising (i) a subset of barcoded nucleic acid strands of the first set bound to (ii) a subset of barcoded nucleic acid strands of the second set to form a unique nucleic acid barcode.

In some embodiments, the barcoded nucleic acid strands of the first set comprise, optionally in the 5' to 3' direction: a promoter sequence, a sequencing adaptor sequence, a first barcode sequence and a first anchor sequence. In some embodiments, the barcoded nucleic acid strands of the second set comprise, in the 5' to 3' direction: a polyT sequence, a unique molecular identifier sequence, a second barcode sequence and a second anchor sequence, wherein the second anchor sequence is complementary to the first anchor sequence.

In some embodiments, the method further comprises hybridizing the second set of barcoded nucleic acid strands to the first set of barcoded nucleic acid strands and producing patches that comprise partially double-stranded barcoded nucleic acids.

In some embodiments, the method further comprises combining the array of overlapping patches with a polymerase, a primer that binds to the second barcode sequence, and dNTPs, and producing a nucleic acid strand comprising, in the 5' to 3' direction: a promoter sequence, a sequencing adaptor sequence, a first barcode sequence, a first anchor sequence, a second barcode sequence, a unique molecular identifier sequence and a polyT sequence.

In some embodiments, the method further comprises removing from the array of overlapping patches the second set of barcoded nucleic acid.

In some embodiments, the method further comprises flow patterning and immobilizing onto the surface of the substrate a set of molecular binding partners of a third solution to produce columns that are parallel to and space apart relative to each other and relative to the columns of (b), wherein each column comprises Z patches of molecular binding partners, wherein each column comprises a different molecular binding partner, and wherein Z is a number greater than 2, In some embodiments, the method further comprises coupling a microwell array to the surface of the substrate to produce a device, wherein each microwell of the microwell array comprises a patch that includes a unique nucleic acid barcode and optionally at least one antibody.

In some embodiments, the first and/or second set of barcoded nucleic acid strands and/or molecular binding partners (e.g., antibodies) are patterned and immobilized onto the surface of the substrate using a microfluidic flow patterning chip.

Also provided herein is a polyomic multiplexing device, comprising at least 20 (e.g., at least 50, at least 100, at least 1000, at least 10000, or at least 20000) enclosed microwells formed by a substrate coupled to a microwell array, wherein each microwell of the device comprises a unique molecular barcode immobilized on the substrate, wherein each unique molecular barcode comprises (a) a first patch that comprises a first antibody, wherein the first patch is adjacent to (b) a second patch that comprises a second antibody, wherein the second patch is adjacent to (c) a third patch that comprises a unique nucleic acid barcode that optionally comprises a terminal polyT sequence, wherein the third patch is adjacent to (d) a fourth patch that comprises a third antibody, wherein the fourth patch is adjacent to (f) a fifth patch that comprises a fourth antibody, wherein the first antibody is of the same type as the fourth antibody, and the second antibody is of the same type as the third antibody. In some embodiments, the unique molecular barcode further comprises (g) a sixth patch that comprises a fifth antibody and (h) a seventh patch that comprises a sixth antibody, wherein the fifth antibody is of the same type as the sixth antibody.

In some embodiments, microwells of the device comprise a single cell or a single subset (e.g., 2 or 3) cells. The cells may be obtained from a biological sample, such as a blood, urine, or saliva sample. Other biological samples are encompassed herein.

In some embodiments, 100 to 1000 (e.g., 100, 200, 300, 400, 500, 600, 700, 800, 900, or 1000) cells are assayed (e.g., for the presence of particular nucleic acids and/or antibodies) using a single device as provided herein.

BRIEF DESCRIPTION OF THE DRAWINGS

FIG. 3: Barcode immobilization reactions. The oligonucleotide sequence including T7 promoter, sequencing adapter and row barcodes (Barcodes A) are patterned and immobilized on glass surface using the first microfluidic flow patterning chip. Afterwards, the column barcode sequences (Barcodes B) are hybridized and extended through primer extension reaction. The reactions are quenched with sodium hydroxide to strip off the shorter second strand, and complete the molecular barcodes terminal with poly(dT) sequences. The barcode sequences are known a priori to enable deterministic barcoding.

FIG. 4: Flow patterning of molecular barcodes confirmed by fluorescently-labeled hybridization probes. Immobilization of row barcodes (Barcodes A, top left). Patterning and extension of column barcodes confirmed by a fluorescently labeled hybridization probe against the poly(dT) sequences (top right) illustrating the barcoded patches. Distinct barcode sequences are quality checked using fluorescently labeled hybridization probes against the specific barcode sequences against row barcode 20 (bottom right) and column barcode 19 (bottom right). Only the oligonucleotide sequences carrying column 19 and row 20 barcode sequences are specifically labeled.

FIG. 13: Combining multiple omics analyses via deterministic barcoding. Example 1: single-cell transcriptome and microRNA co-analysis. Left: Schematic depiction of cell loading and device assembly, and on-chip cell lysis.

Right: Use of upper and lower slides for microRNA and transcriptome measurement of the same single cells. The mechanism that microRNAs and mRNAs can be linked and associated to the same single cell is due to the deterministic molecular barcoding, in which the sequence and location of each molecular barcode in each microchamber (microwell) is known.

FIGS. 14A-14B: Combining polyomics analyses via deterministic barcoding. Example 2: co-detection of whole transcriptome and a panel of proteins either secreted from the cell (FIG. 14A) or intracellular/surface proteins released after cell lysis (FIG. 14B). The former is conducted using the aforementioned molecular barcode approach with the lower glass slides containing molecular barcode micropatch array. The latter is conducted with an array of antibody features patterned on the top glass slide. The mechanism that proteins and mRNAs can be linked and associated to the same single cell is due to the deterministic molecular barcoding, in which the sequence and location of each molecular barcode in each microchamber is known.

Figure 15A:
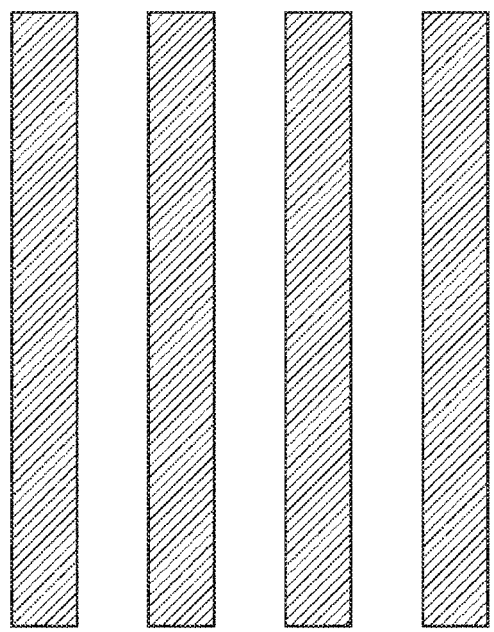
Figure 15B:
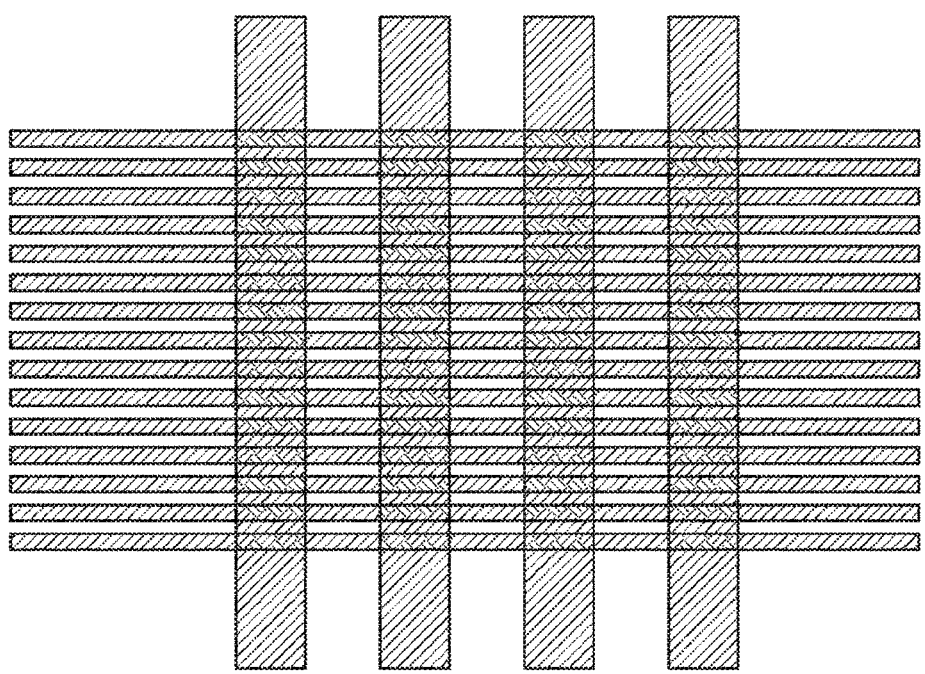
Figure 15C:
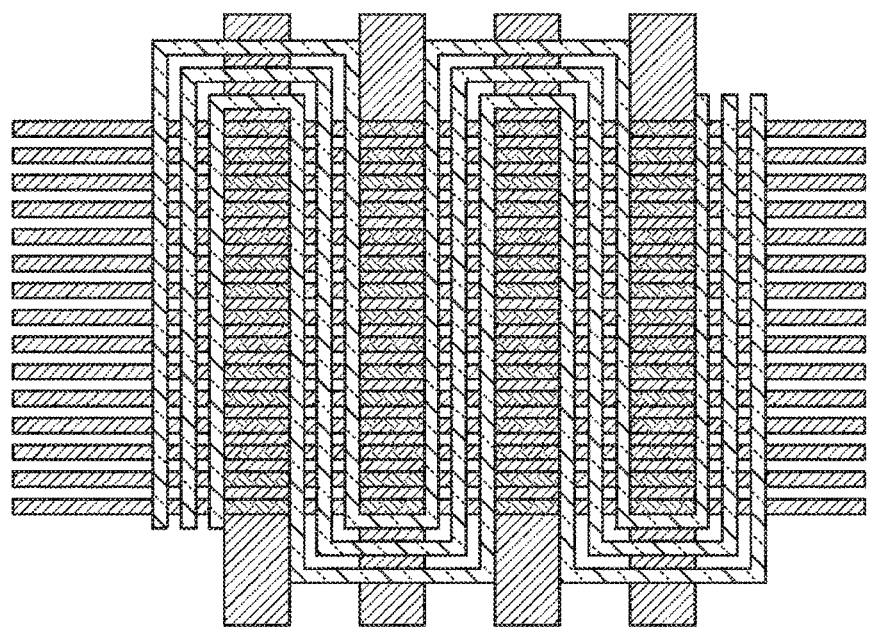
Figure 15D:
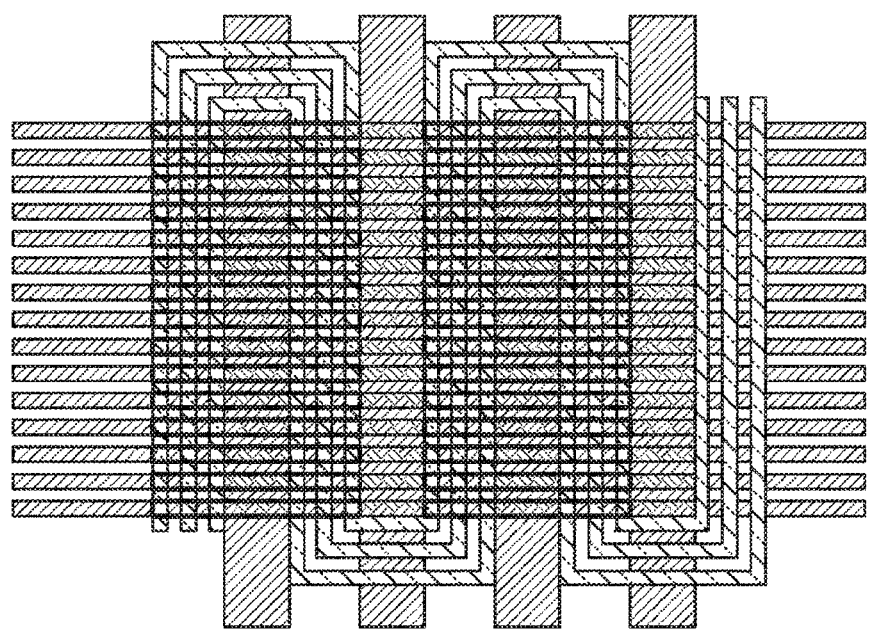

FIGS. 15A-15D depict an example of a device of the present disclosure, which include a substrate comprising columns of barcoded nucleic acids of a first subset (FIG. 15A), rows of barcoded nucleic acids of a second subset (FIG. 15B), additional columns (formed by a 'wavy' flow pattern) of subsets of different antibodies (FIG. 15C), and microwells coupled to the substrate (black squares) (FIG. 15C).

DETAILED DESCRIPTION

Single-cell sequencing, in particular, sequencing of a whole transcriptome for gene expression profiling and phenotype analysis, is an enabling scientific discovery tool in nearly all fields of biology. Nonetheless, several major problems still exist. First, in order to quantitatively dissect phenotypic and functional heterogeneity of complex cell populations, one must simultaneously sequence more than 10,000 single cells. To date, there is no technology to achieve this goal. Second, in order to be utilized in the clinical setting, the technology should work for low-input samples (e.g., <50,000 cells) and rare cell populations isolated from clinical specimens. Third, the field is still unable to measure polyomics information in the same cell, for example, to directly correlate gene expression (transcriptome sequencing) to regulatory elements (e.g., microRNAs, epigenetic modification), which is important for understanding the mechanism of cellular heterogeneity. The technology of the present disclosure addresses the three foregoing problems.

Methods

Provided herein are methods of producing a barcoded array, comprising (a) flow patterning and immobilizing onto a surface of a substrate a first set of barcoded nucleic acid (e.g., DNA) strands of a first solution to produce columns that are parallel to and space apart relative to each other, wherein each column comprises X patches of barcoded nucleic acid strands of the first set, wherein the patches within each column are spaced apart relative to each other, wherein each column comprises a different subset of barcoded nucleic acid strands, and wherein X is a number greater than 2; and (b) flow patterning and immobilizing onto the surface of the substrate a second set of barcoded nucleic acid (e.g., DNA) strands of a second solution to produce rows that are parallel to and space apart relative to each other, wherein each row comprises Y patches of barcoded nucleic acid strands of the second set, wherein the patches within each row are spaced apart relative to each other, wherein each row comprises a different subset of barcoded nucleic acid strands, wherein the rows are perpendicular relative to the columns, and wherein Y is a number greater than 2, thereby producing a X*Y array of overlapping patches, each overlapping patch comprising (i) a subset of barcoded nucleic acid strands of the first set and (ii) a subset of barcoded nucleic acid strands of the second set.

General methods of flow patterning are known, and include, for example, streamline flow patterning, which is the flow of fluid in which its velocity at any point is constant or varies in a regular manner.

In some embodiments, the barcoded nucleic acid strands of the first set comprise, in the 5' to 3' direction: a promoter sequence, a sequencing adaptor sequence, a first barcode sequence and a first anchor sequence. In some embodiments, the barcoded nucleic acid strands of the first set comprise, in the 3' to 5' direction: a promoter sequence, a sequencing adaptor sequence ("sequencing adaptor"), a first barcode sequence and a first anchor sequence.

Promoter sequences are DNA sequences that define where transcription of a gene or other downstream nucleotide sequence by polymerase (e.g., RNA polymerase) begins. Examples of promoter sequences include, but are not limited to, T7 promoter sequences, T3 promoter sequences, and SP6 promoter sequences.

Sequence adaptors are short (known) nucleotide (e.g., DNA) sequences added to an end of a nucleic acid of interest. A complementary sequencing primer binds to the sequence adaptor. The length of a sequence adaptor may vary. For example, a sequence adaptor may have a length of 10 to 50 nucleotide. In some embodiments, a sequence adaptor has a length of 10, 20, 30, 40, or 50 nucleotides.

Anchor sequences enable binding of barcoded nucleic acids to each other. As shown in FIG. 3 (Step 2), Barcode A has an anchor sequence, and Barcode B has an anchor sequence that is complementary to the anchor sequence of Barcode A such that Barcode A and B can bind to each other.

Figure 1:
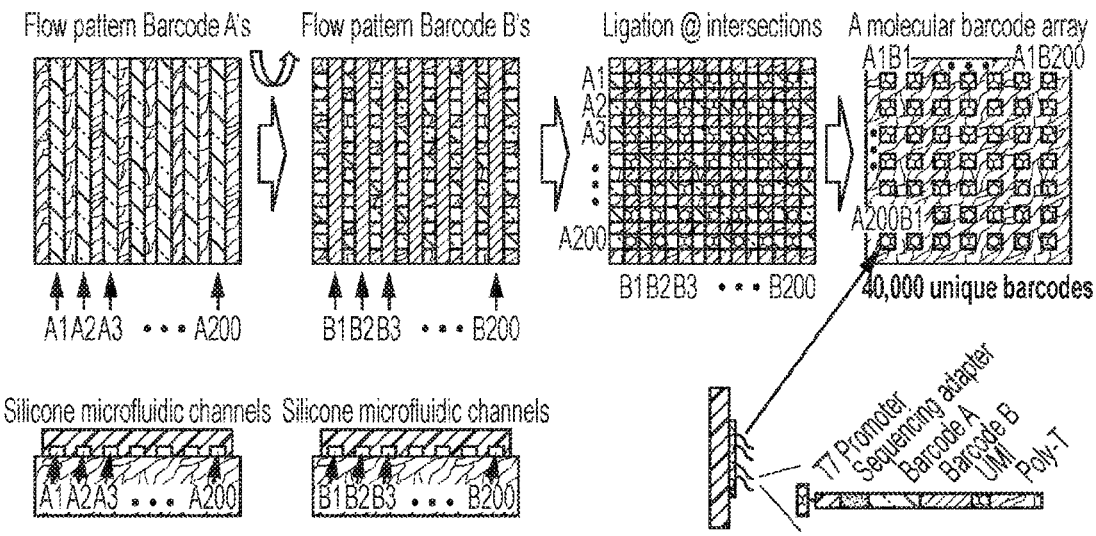
FIG. 1: Design and fabrication of a large-scale array of distinct molecular barcode patches (40,000 per chip) for single-cell transcriptome capture. The upper images illustrate an example flow patterning fabrication process. The lower left images show a cross-sectional view of microchannel-guided flow patterning. The lower right images shows an examples of composite molecular barcodes combining Barcode A, Barcode B and other sequences (e.g., promoter, sequencing adaptor, unique molecular identifier (UMI) and polyT sequence).

A barcode sequence is a sequence of nucleotides (e.g., deoxyribonucleotides) that is specific to a set or a subset of nucleic acids strands. For example, as shown in FIG. 1, the nucleic acid strands of subset A1 (of Barcode A) are coded with a specific barcode sequence, while subsets A2, A3, A4, etc. are each coded with a different barcode sequence, each barcode specific to the subset. Likewise, the nucleic acid strands of subset B1 (of Barcode B) are coded with a specific barcode sequence, while subsets B2, B3, B4, etc. are each coded with a different barcode sequence, each barcode specific to the subset. Thus, each overlapping patch, which includes a unique combination of Barcode A subsets and Barcode B subsets, contains a unique composite barcode (Barcode A+Barcode B). For example, an overlapping patch containing A1+B1 barcodes is uniquely coded relative to its neighboring overlapping patches, which contain A2+B1 barcodes, A1+B2 barcodes, A2+B2 barcodes, etc., as depicted in FIG. 1.

In some embodiments, the barcoded nucleic acid strands of the second set comprise, in the 5' to 3' direction: a polyT sequence (e.g., T19V), a unique molecular identifier (UMI) sequence, a second barcode sequence and a second anchor sequence, wherein the second anchor sequence is complementary to the first anchor sequence. In some embodiments, the barcoded nucleic acid strands of the second set comprise, in the 3' to 5' direction: a polyT sequence, a unique molecular identifier sequence, a second barcode sequence and a second anchor sequence, wherein the second anchor sequence is complementary to the first anchor sequence.

Examples of UMIs are described by Kivioja T et al. *Nature Methods* 9, 72-74 (2012), incorporated herein by reference.

The methods may further comprise maintaining (incubating) the array of overlapping patches under conditions that result in hybridization of the second set of barcoded nucleic acid strands to the first set of barcoded nucleic acid strands to produce patches that comprise partially double-stranded barcoded nucleic acids. Nucleic acid hybridization conditions are known.

The methods may also comprise maintaining the array of overlapping patches in the presence of a polymerase, a primer that binds to the second barcode sequence, and dNTPs (e.g., dATP, dTTP, dCTP, and dGTP), under conditions that result in DNA polymerization (production/synthesis of strand of DNA) to produce a nucleic acid strand comprising (e.g., in the 5' to 3' direction): a promoter sequence, a sequencing adaptor sequence, a first barcode sequence, a first anchor sequence, a second barcode sequence, a unique molecular identifier sequence and a polyT sequence. Nucleic acid synthesis conditions are known.

In some embodiments, the methods comprise removing (e.g., washing) from the array of overlapping patches the second set of barcoded nucleic acid. In some embodiments, the polymerization/synthesis reaction is quenched with sodium hydroxide to strip off the shorter second barcoded nucleic acid strand, The surface may be a glass surface, a silicon surface or a silica surface. Other surfaces are encompassed by the present disclosure. In some embodiments, the glass surface is coated with poly-1-lysine.

In some embodiments, the substrate is a microwell array or is coupled to a microwell array, and wherein each overlapping patch occupies or is aligned with a single microwell of the microwell array.

In some embodiments, X equals 20-20,000. For example, X may equal 20-50, 20-100, 20-500, 20-1000, 20-5000, 20-10000, 50-100, 50, 500, 50-1000, 50-5000, 50-10000, 50-20000, 100-500, 100-1000, 100-5000, 100-10000, or 100-20000. In some embodiments, X equals 100-20,000.

In some embodiments, Y equals 20-20,000. For example, Y may equal 20-50, 20-100, 20-500, 20-1000, 20-5000, 20-10000, 50-100, 50, 500, 50-1000, 50-5000, 50-10000, 50-20000, 100-500, 100-1000, 100-5000, 100-10000, or 100-20000. In some embodiments, Y equals 100-20,000.

At least one (e.g., at least 2, 3, 4, 5, 10, 20) column, or each (all) row, may have a width of 10-500 microns, or 50-200 microns. For example, a column may have a width of 10, 20, 30, 40, 50, 60, 70, 80, 90, 100, 110, 120, 130, 140, 150, 160, 170, 180, 190 or 200 microns. In some embodiments, a column has a width of 100 microns.

At least one (e.g., at least 2, 3, 4, 5, 10, 20) column, or each (all) row, may have a width of 10-500 microns, or 50-200 microns. For example, a row may have a width of 10, 20, 30, 40, 50, 60, 70, 80, 90, 100, 110, 120, 130, 140, 150, 160, 170, 180, 190 or 200 microns. In some embodiments, a row has a width of 100 microns.

Typically, at least one, or each (all), overlapping patch has an area of 100-40,000 $\mu m^2$. For example, an overlapping path may have an area of 100, 200, 300, 400, 500, 600, 700, 800, 900, 1000, 2000, 3000, 4000, 5000, 6000, 7000, 8000, 9000, 10000, 20000, 30000 or 40000 $\mu m^2$. In some embodiments, an overlapping patch has an area of 10,000 $\mu m^2$. Thus, in some embodiments, the dimensions of a patch may be 10×10 $\mu m$ to 200×200 $\mu m$. Larger or smaller overlapping patches are encompassed by the present disclosure.

In some embodiments, the overlapping patches within a single row are separated from each other by 10-500 microns, or 20-200 microns. For example, the overlapping patches within a single row may be separated from each other by 10, 20, 30, 40, 50, 60, 70, 80, 90, 100, 125, 150, 175 or 200 microns. In some embodiments, the overlapping patches within a single row are separated from each other by 100 microns.

In some embodiments, the overlapping patches within a single column are separated from each other by 10-500 microns, or 20-200 microns. For example, the overlapping patches within a single column may be separated from each other by 10, 20, 30, 40, 50, 60, 70, 80, 90, 100, 125, 150, 175 or 200 microns. In some embodiments, the overlapping patches within a single column are separated from each other by 100 microns.

In some embodiments, the overlapping patches between adjacent rows are separated from each other by 20-200 microns. For example, the overlapping patches between adjacent rows may be separated from each other by 20, 50, 75, 100, 125, 150, 175 or 200 microns. In some embodiments, the overlapping patches between adjacent rows are separated from each other by 20-30, 20-50, 20-100, 50-100 or 50-200 microns. In some embodiments, the overlapping patches between adjacent rows are separated from each other by (about) 100 microns.

In some embodiments, the overlapping patches between adjacent columns are separated from each other by 20-200 microns. For example, the overlapping patches between adjacent columns may be separated from each other by 20, 50, 75, 100, 125, 150, 175 or 200 microns. In some embodiments, the overlapping patches between adjacent columns are separated from each other by 20-30, 20-50, 20-100, 50-100 or 50-200 microns. In some embodiments, the overlapping patches between adjacent columns are separated from each other by (about) 100 microns.

Figure 2:
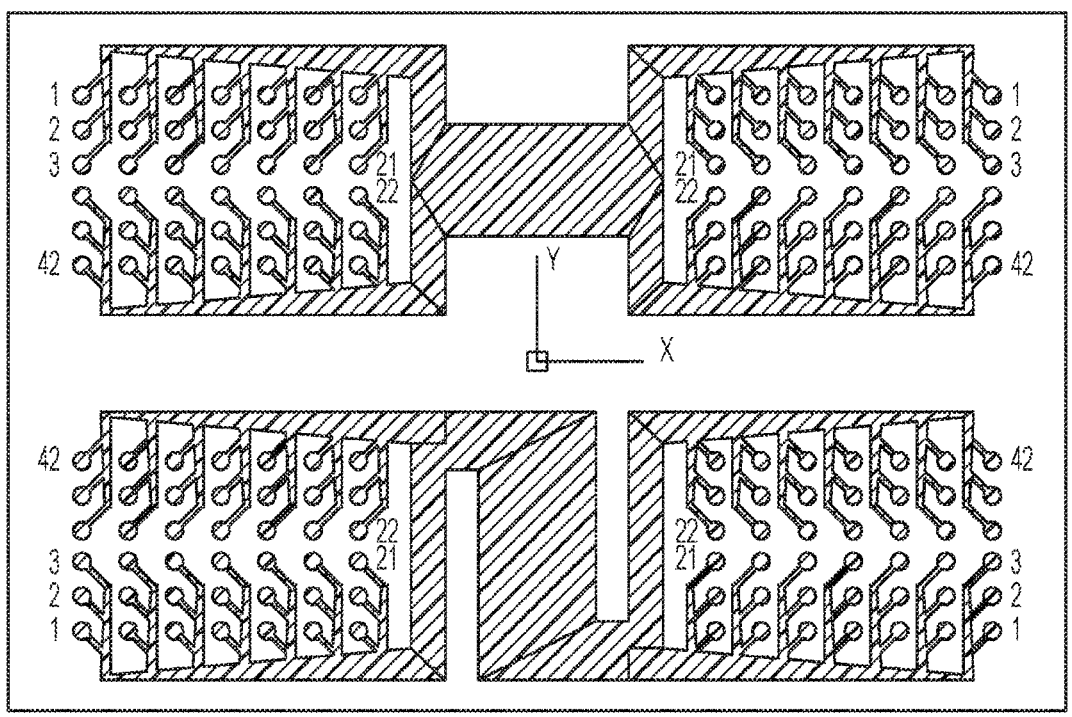
FIG. 2: Microfluidic flow patterning chips designed to produce molecular barcode patches. This examples includes a 42×42 array (throughput ~300-600 single cells) with 100 micron flow-patterning channels (barcoded patches are 100× 100 µm$^2$). The corresponding microwells are separated from each other by 100 µm such that no two wells can share the same barcode.

The first set of barcoded nucleic acid strands may be patterned and immobilized onto the surface of the substrate using, for example, a microfluidic flow patterning chip (see, e.g., FIG. 2). Likewise, the second set of barcoded nucleic acid strands may be patterned and immobilized onto the surface of the substrate using, for example, a microfluidic flow patterning chip (see, e.g., FIG. 2).

Barcoded Arrays and Multiplexing Devices

Also provided herein are barcoded arrays, for example, produced by any of the methods described herein. For example, a barcoded array may be produced by a method, comprising: (a) flow patterning and immobilizing onto a surface of a substrate a first set of barcoded nucleic acid strands of a first solution to produce columns that are parallel to and space apart relative to each other, wherein each column comprises X patches of barcoded nucleic acid strands of the first set, wherein the patches within each column are spaced apart relative to each other, wherein each column comprises a different subset of barcoded nucleic acid strands, and wherein X is a number greater than 2; and (b) flow patterning and immobilizing onto the surface of the substrate a second set of barcoded nucleic acid strands of a second solution to produce rows that are parallel to and space apart relative to each other, wherein each row comprises Y patches of barcoded nucleic acid strands of the second set, wherein the patches within each row are spaced apart relative to each other, wherein each row comprises a different subset of barcoded nucleic acid strands, wherein the rows are perpendicular relative to the columns, and wherein Y is a number greater than 2, thereby producing a X*Y array of overlapping patches, each overlapping patch comprising (i) a subset of barcoded nucleic acid strands of the first set and (ii) a subset of barcoded nucleic acid strands of the second set.

Also provided herein are multiplexing devices comprising the barcoded array coupled to a microwell array, wherein each overlapping patch is aligned with a single microwell of the array such that each overlapping patch corresponds to a single microwell.

Further provided herein are multiplexing devices comprising a barcoded array, wherein the substrate is a microwell array, and wherein each overlapping patch occupies a single microwell of the microwell array.

In some embodiments, each microwell of the microwell array contains no more than 5 cells. For example, each microwell of the microwell array may contain no more than 4, no more than 3, or no more than 2 cells. In some embodiments, each microwell of the microwell array contains no more than 2 cells. some embodiments, each microwell of the microwell contains a single cell.

The microwell array may be located, for example, between the barcoded array and another substrate such that microwells of the microarray are sealed (e.g., fluid cannot leave or enter the microwell).

In some embodiments, the other substrate is coated with dried (e.g., lyophilized) lysis buffer.

In some embodiments, the other substrate comprises a nucleic acid capture array, such as a microRNA capture array.

In some embodiments, the other substrate comprises an antibody capture array (see, e.g., U.S. Pat. No. 9,188,586, incorporated herein by reference).

The present disclosure further encompasses the embodiments described in the following numbered paragraphs:

1. A method of producing a barcoded array, comprising:
(a) flow patterning and immobilizing onto a surface of a substrate a first set of barcoded nucleic acid strands of a first solution to produce columns that are parallel to and space apart relative to each other, wherein each column comprises X patches of barcoded nucleic acid strands of the first set, wherein the patches within each column are spaced apart relative to each other, wherein each column comprises a different subset of barcoded nucleic acid strands, and wherein X is a number greater than 2;
(b) flow patterning and immobilizing onto the surface of the substrate a second set of barcoded nucleic acid strands of a second solution to produce rows that are parallel to and space apart relative to each other, wherein each row comprises Y patches of barcoded nucleic acid strands of the second set, wherein the patches within each row are spaced apart relative to each other, wherein each row comprises a different subset of barcoded nucleic acid strands, wherein the rows are perpendicular relative to the columns, and wherein Y is a number greater than 2,
thereby producing a X*Y array of overlapping patches, each overlapping patch comprising (i) a subset of barcoded nucleic acid strands of the first set and (ii) a subset of barcoded nucleic acid strands of the second set.

2. The method of paragraph 1, wherein the barcoded nucleic acid strands of the first set comprise, optionally in the 5' to 3' direction: a promoter sequence, a sequencing adaptor sequence, a first barcode sequence and a first anchor sequence.

3. The method of paragraph 1 or 2, wherein the barcoded nucleic acid strands of the second set comprise, in the 5' to 3' direction: a polyT sequence, a unique molecular identifier sequence, a second barcode sequence and a second anchor sequence, wherein the second anchor sequence is complementary to the first anchor sequence.

4. The method of any one of paragraphs 1-3, further comprising maintaining the array of overlapping patches under conditions that result in hybridization of the second set of barcoded nucleic acid strands to the first set of barcoded nucleic acid strands to produce patches that comprise partially double-stranded barcoded nucleic acids.

5. The method of paragraph 4, further comprising maintaining the array of overlapping patches in the presence of a polymerase, a primer that binds to the second barcode sequence, and dNTPs, under conditions that result in DNA polymerization to produce a nucleic acid strand comprising, in the 5' to 3' direction: a promoter sequence, a sequencing adaptor sequence, a first barcode sequence, a first anchor sequence, a second barcode sequence, a unique molecular identifier sequence and a polyT sequence.

6. The method of paragraph 5 further comprising removing from the array of overlapping patches the second set of barcoded nucleic acid.

7. The method of any one of paragraphs 1-6, wherein the surface is a glass surface, silicon or silica.

8. The method of paragraph 7, wherein the glass surface is coated with poly-1-lysine.

9. The method of any one of paragraph 1-6, wherein the substrate is a microwell array, and were each overlapping patch occupies a single microwell of the microwell array.

10. The method of any one of paragraphs 1-9, wherein X equals 20-20,000 and/or Y equals 20-20,000.

11. The method of paragraph 10, wherein X equals 100-20,000 and/or Y equals 100-20,000.

12. The method of paragraph 11, wherein X equals 1000-20,000 and/or Y equals 1000-20,000.

13. The method of paragraph 12, wherein X equals 10,000-20,000 and/or Y equals 10,000-20,000.

14. The method of any one of paragraphs 1-13, wherein each column and/or row has a width of 50-200 microns.

15. The method of paragraph 14, wherein each column and/or row has a width of 100 microns.

16. The method of any one of paragraphs 1-15, wherein each overlapping patch has an area of 400-40,000 $\mu m^2$.

17. The method of paragraph 16, wherein each overlapping patch has an area of 10,000 $\mu m^2$.

18. The method of any one of paragraphs 1-17, wherein the overlapping patches within a single row and/or within a single column are separated from each other by 20-200 microns.

19. The method of paragraph 18, wherein the overlapping patches within a single row and/or within a single column are separated from each other by 100 microns.

20. The method of any one of paragraphs 1-19, wherein the overlapping patches between adjacent rows and/or between adjacent columns are separated from each other by 20-200 microns.

21. The method of paragraph 20, wherein the overlapping patches between adjacent rows and/or between adjacent columns are separated from each other by 100 microns.

22. The method of any one of paragraphs 1-21, wherein the first and/or second set of barcoded nucleic acid strands are patterned and immobilized onto the surface of the substrate using a microfluidic flow patterning chip.

23. A barcoded array produced by a method, comprising:
(a) flow patterning and immobilizing onto a surface of a substrate a first set of barcoded nucleic acid strands of a first solution to produce columns that are parallel to and space apart relative to each other, wherein each column comprises X patches of barcoded nucleic acid strands of the first set, wherein the patches within each column are spaced apart relative to each other, wherein each column comprises a different subset of barcoded nucleic acid strands, and wherein X is a number greater than 2;

(b) flow patterning and immobilizing onto the surface of the substrate a second set of barcoded nucleic acid strands of a second solution to produce rows that are parallel to and space apart relative to each other, wherein each row comprises Y patches of barcoded nucleic acid strands of the second set, wherein the patches within each row are spaced apart relative to each other, wherein each row comprises a different subset of barcoded nucleic acid strands, wherein the rows are perpendicular relative to the columns, and wherein Y is a number greater than 2, thereby producing a X*Y array of overlapping patches, each overlapping patch comprising (i) a subset of barcoded nucleic acid strands of the first set and (ii) a subset of barcoded nucleic acid strands of the second set.

24. The barcoded array of claim 23, wherein the barcoded nucleic acid strands of the first set comprise, optionally in the 5' to 3' direction: a promoter sequence, a sequencing adaptor sequence, a first barcode sequence and a first anchor sequence.

25. The barcoded array of claim 23 or 24, wherein the barcoded nucleic acid strands of the second set comprise, in the 5' to 3' direction: a polyT sequence, a unique molecular identifier sequence, a second barcode sequence and a second anchor sequence, wherein the second anchor sequence is complementary to the first anchor sequence.

26. The barcoded array of any one of claims 23-25, further comprising hybridizing the second set of barcoded nucleic acid strands to the first set of barcoded nucleic acid strands and producing patches that comprise partially double-stranded barcoded nucleic acids.

27. The barcoded array of claim 26, further comprising combining the array of overlapping patches with a polymerase, a primer that binds to the second barcode sequence, and dNTPs, and producing a nucleic acid strand comprising, in the 5' to 3' direction: a promoter sequence, a sequencing adaptor sequence, a first barcode sequence, a first anchor sequence, a second barcode sequence, a unique molecular identifier sequence and a polyT sequence.

28. The barcoded array of claim 27 further comprising removing from the array of overlapping patches the second set of barcoded nucleic acid.

29. The barcoded array of any one of claims 23-28, wherein the surface is a glass surface, silicon or silica.

30. The barcoded array of claim 9, wherein the glass surface is coated with poly-1-lysine.

31. The barcoded array of any one of claim 23-30, further comprising applying a microwell array to the surface of the substrate to produce a device wherein each overlapping patch, each row or overlapping patches, or each column of overlapping patches occupies a single microwell of the microwell array.

32. The barcoded array of any one of claims 23-31, wherein X equals 20-20,000 and/or Y equals 20-20,000, X equals 100-20,000 and/or Y equals 100-20,000, X equals 1000-20,000 and/or Y equals 1000-20,000, or X equals 10,000-20,000 and/or Y equals 10,000-20,000.

33. The barcoded array of any one of claims 23-32, wherein each column and/or row has a width of 50-200 microns, or each column and/or row has a width of 100 microns.

34. The barcoded array of any one of claims 23-33, wherein each overlapping patch has an area of 400-40,000 $\mu m^2$, or each overlapping patch has an area of 10,000 $\mu m^2$.

35. The barcoded array of any one of claims 23-34, wherein the overlapping patches within a single row and/or within a single column are separated from each other by 20-200 microns, or the overlapping patches within a single row and/or within a single column are separated from each other by 100 microns.

36. The barcoded array of any one of claims 23-35, wherein the overlapping patches between adjacent rows and/or between adjacent columns are separated from each other by 20-200 microns, or the overlapping patches between adjacent rows and/or between adjacent columns are separated from each other by 100 microns.

37. The barcoded array of any one of claims 23-36, wherein the first and/or second set of barcoded nucleic acid strands are patterned and immobilized onto the surface of the substrate using a microfluidic flow patterning chip.

38. A multiplexing device comprising the barcoded array of any one of paragraphs 23-37 coupled to a microwell array, wherein each overlapping patch is aligned with a single microwell of the array such that each overlapping patch corresponds to a single microwell.

39. A multiplexing device comprising the barcoded array of any one of paragraphs 23-37, wherein the substrate is a microwell array, and wherein each overlapping patch occupies a single microwell of the microwell array.

40. The multiplexing device of paragraph 38 or 39, wherein each microwell of the microwell array contains no more than 5 cells.

41. The multiplexing device of paragraph 40, wherein each microwell of the microwell array contains no more than 2 cells.

42. The multiplexing device of paragraph 41, wherein each microwell of the microwell array contains a single cell.

43. The multiplexing device of any one of paragraphs 23-42, wherein the microwell array is located between the barcoded array and another substrate such that microwells of the microarray are sealed.

44. The multiplexing device of paragraph 43, wherein the other substrate is coated with lyophilized lysis buffer.

45. The multiplexing device of paragraph 43 or 44, wherein the other substrate comprises a nucleic acid capture array.

46. The multiplexing device of paragraph 45, wherein the nucleic acid capture array is a microRNA capture array.

47. The multiplexing device of paragraph 45, wherein the other substrate comprises an antibody capture array.

EXAMPLES

Example 1. Fabrication of a High-Density Array Comprising 40,000 Distinct Molecular Barcodes Two hundred unique DNA barcodes (FIG. 1, Barcode A's: A1, A2, A3 . . . A200), each having a 5' linker (T7 promoter+sequencing adapter) were immobilized on a substrate using a microfluidic flow patterning technique. The first set of Barcode A molecules (A1-A200; see, e.g., FIG. 3 step 1) were patterned onto a poly-1-lysine-coated glass slide using a microfluidic patterning chip (FIG. 2, top) and incubated overnight to form "Barcode A stripes". The barcode concentration was greater than 100 µM in order to attach billions of barcodes corresponding to each single cell. The patterned Barcode A molecules were covalently linked to the glass slide surface by UV exposure and incubation at 80° C. for at least 2 hours. The 3' ends of the immobilized Barcode A molecules were free for subsequent hybridization and extension reactions. After patterning the first set of Barcode A molecules, the original microfluidic chip was removed, and a second microfluidic patterning chip (FIG. 2, bottom) was placed on top of the patterned glass slide with the microchannels perpendicular to the patterned Barcode A stripes to add a second set of Barcodes B molecules (FIG. 1, Barcode B's: B1, B2, B3 . . . B200), each having a poly(dT) sequence at the 3' end for mRNA capture, thereby forming "Barcode B stripes." This was achieved using a primer extension reaction where the Barcode B molecules were first hybridized to the previously patterned Barcode A molecules via a complementary anchor sequence (see, e.g., FIG. 3 step 2). After hybridization for more than 1 hour, the microfluidic patterning chip was removed, unbound barcodes were washed away and the hybridized barcodes were extended by DNA polymerase I (see, e.g., FIG. 3 step 3). The reaction was then quenched with sodium hydroxide to remove the shorter strands (see, e.g., FIG. 3 step 4). The resulting immobilized nucleic acid strand included both Barcode A and Barcode B sequences terminated at the 3' end with a poly(dT) tail for mRNA capture.

An array of 200×200 (40,000) square distinct barcode patches were formed by overlapping Barcode A and Barcode B areas on the slide (intersection of A and B) (FIGS. 1 and 4). This array interfaces with a single-cell-loaded microchamber array for capture of single-cell-derived messenger RNAs for whole transcriptome sequencing. The stripes are 100 um in width and, thus, the barcodes patches are 100 μm X 100 μm. All molecular barcodes were chosen from a validated oligomer library and all the sequences in this database are orthogonal to human mRNAs.

Example 2. Cell Capture Platforms

Figure 5:
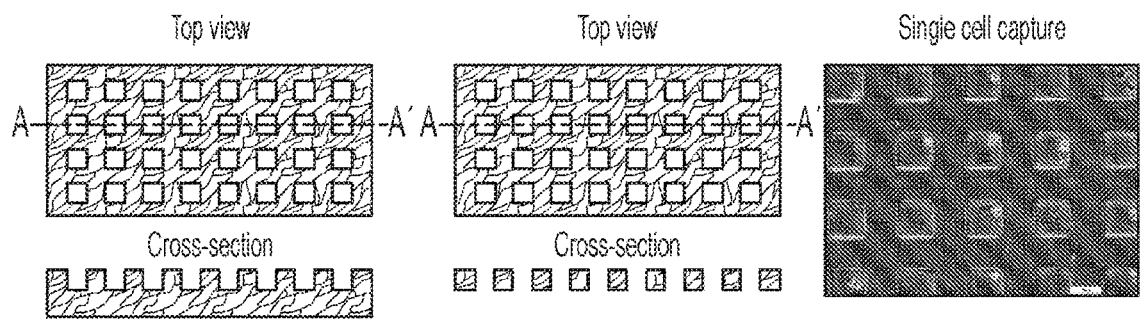
FIG. 5: Microwell array devices used for single cell capture. In one example, wells are created on the surface of a substrate (left image). In another example, a through-hole microwell array was created on a thin substrate (middle and right images). Substrates can be glass, polymer or plastic.

Microwell devices (individual wells~picoliter to nanoliter volume) were used as single cell capture platforms. Two types of microwell devices were used (FIG. 5). The first device has microwells created on the surface of a substrate (glass, polymer or plastic). This device can be used with the alignment-free strategy described in Example 3. The second device is a through-hole microwell array created in a thin substrate (glass, polymer or plastic) which can be used with the deterministic alignment strategy described in Example 4.

Example 3. An Alignment-Free Strategy for Interfacing Single Cells with a High-Density Barcode Array For reliable mRNA capture from single cells using the high density barcode array, each barcoded patch is interfaced with a single cell. At least two techniques may be used to interface the microwell device with a barcode array: an alignment-free technique, described in this Example, and a deterministic alignment technique, described in Example 4.

Figure 6:
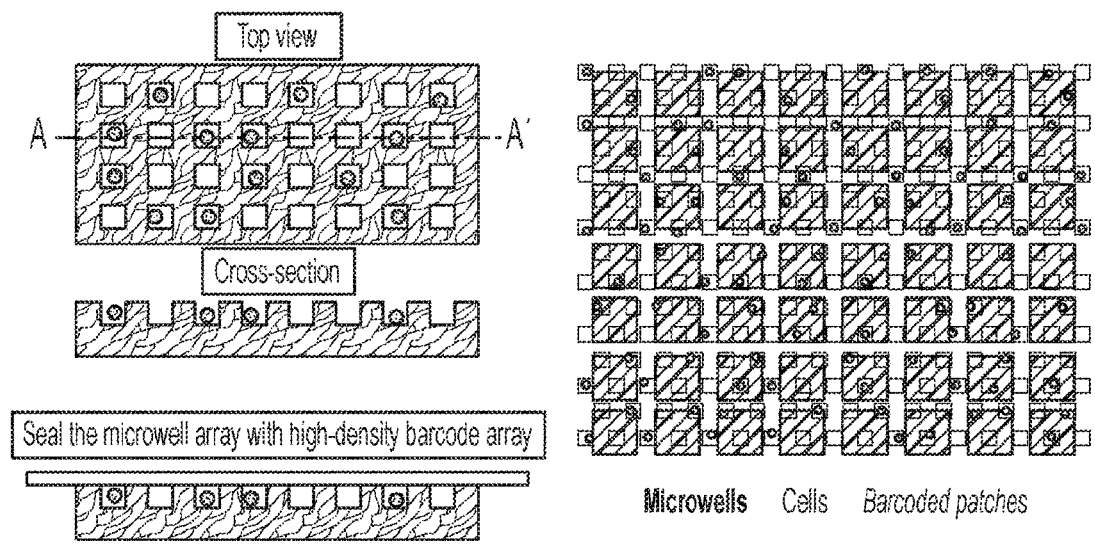
FIG. 6: Alignment-free strategy for interfacing high-density barcode array with single cells. Microwells are loaded randomly with cells such that ~50-70% of the wells are occupied with single cells. The microwells are then sealed with barcode array without alignment. After mechanical clamping to stabilize the seal, fluorescence and brightfield images are taken to determine the well and barcoded patch locations. Patches are patterned such that one patch can only contain up to 4 wells at most. This alignment-free approach yields ~10-30% single cell correspondence with the distinctly barcoded patches.

With the alignment-free technique, the first version of microwell arrays is used, and the microwell dimensions and cell loading protocols are set such that when the high-density barcode array is randomly overlaid on top of the microwell devices, 10-30% of the barcodes were interfaced with single cells (FIG. 6). The microwell dimensions and cell loading densities are chosen such that when cells are randomly loaded into microwells, 50-60% of the wells receive a single cell while the rest either remains empty or receives more than one cell (based on Poisson distribution). The size of wells is also such that only 1 to 4 individual wells can fit into a footprint of 100×100 μm² region (corresponding to the size of barcoded patches). With these dimensions, when the high-density barcode array is overlaid on top of the microwell device without alignment, 10-30% of the barcoded patches are interfaced with single cells, while the rest of the barcodes either get no cell or more than one cell. The barcode locations corresponding to the single cells are recorded using imaging. For this purpose, the barcoded oligos are pre-tagged with a fluorophore labeled hybridization probe and their locations are determined using fluorescence microscopy once the microwell and barcode arrays are overlaid together. Microwell locations are determined using bright field imaging. The corresponding wells and barcodes are matched using a custom software. The overall random cell loading and alignment-free approach enables a straightforward operation to utilize the high-density barcode arrays.

Figure 7:
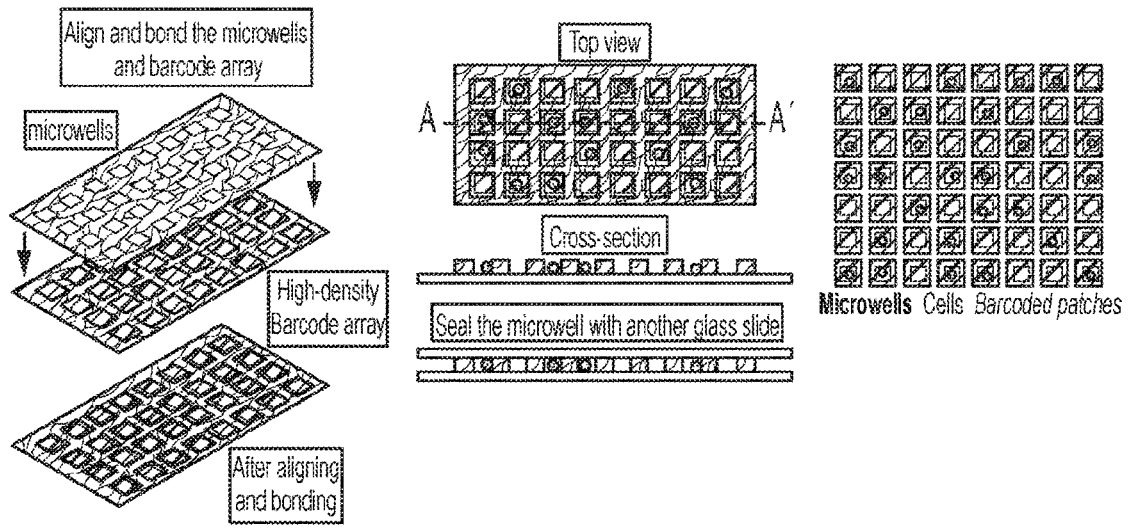
FIG. 7: Deterministic alignment strategy for interfacing a high-density barcode array with single cells. Microwells are fabricated with through-hole wells which are then aligned and bonded with the high-density barcoded array using custom-made alignment platform such that each barcoded patch corresponds to a single well. Once the cells are loaded randomly, microwells are sealed with a second glass slide. After mechanical clamping to stabilize the seal, bright field images are taken to determine the well occupancy and to match barcodes to cells. The expected yield is ~50-70% of the total number of barcoded patches.

Example 4. A Deterministic Alignment Strategy for Interfacing Single Cells with High-Density Barcode Array In this approach, the second version of microwell arrays (through-hole) are used and the microwells are aligned onto the barcode array using a precision alignment tool (FIG. 7). The alignment tool provides translational control in three dimensions (x, y and z) along with rotational control to controllably match the individual microwells to barcode array and bring the two substrates together for bonding. The microwell array is designed with similar pitch size as in a barcode array, such that each barcode patch contains only one microwell after proper alignment. During alignment, the barcode locations are determined using fluorescently labeled probes as described in Example 3, while the microwell locations are determined using the bright field images. Overall, this approach generates a microwell platform where each well is pre-patterned with a distinct barcode. For experiments, cells can be loaded randomly as described Example 3 or using a more deterministic approach as described in Example 5.

Figure 8:
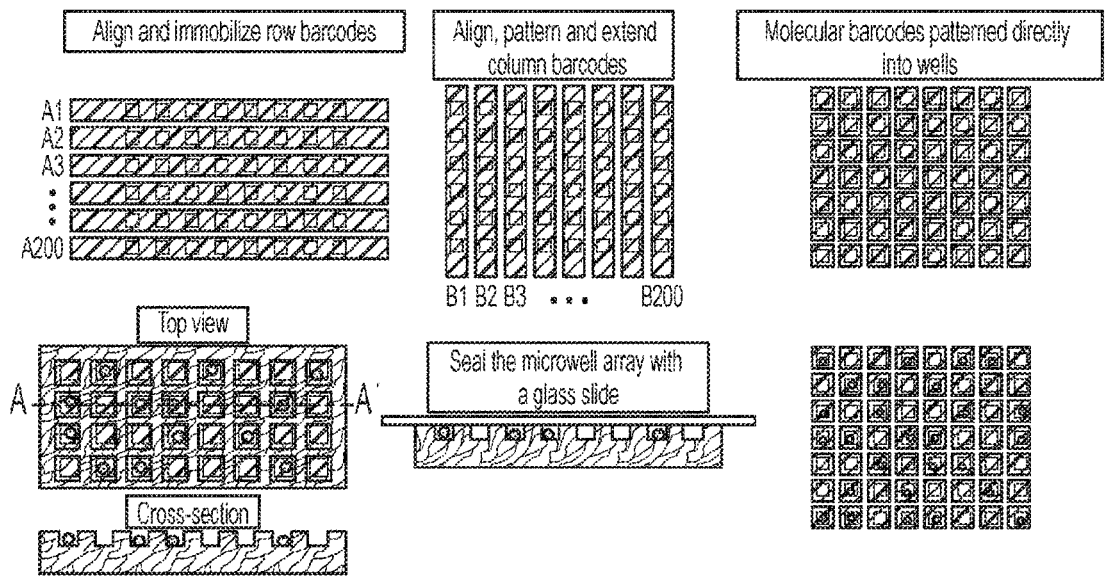
FIG. 8: Alternative deterministic strategy for interfacing high-density barcode array with single cells. Instead of patterning the molecular barcodes onto a flat glass slide, barcodes are patterned and generated onto a microwell platform such that distinct barcodes are directly immobilized within each well. Cell loading and assaying is similar as in other versions.

An alternative deterministic approach was also developed (FIG. 8). Instead of aligning and bonding the through-hole microwells onto barcode array patterned on glass slides, the barcodes A and B are patterned directly onto a microwell array fabricated in different substrates (glass, plastic or polymer) following the similar procedures described in Example 1. For this purpose, the microfluidic flow patterning chips are first aligned onto the microwell arrays such that flow channels are overlaid onto the wells and barcodes are immobilized inside the individual wells. Cell loading can be performed based on random distribution or using a more deterministic approach as in Example 5.

Figure 9:
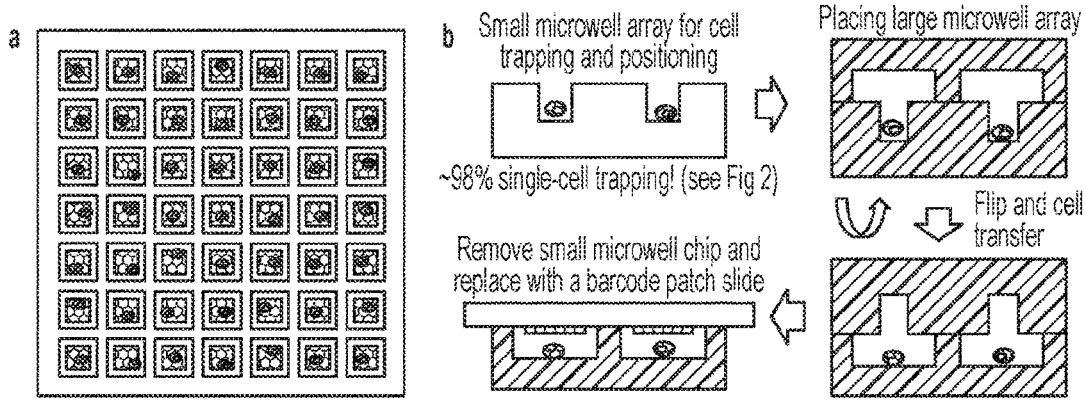
FIG. 9: A cell trapping strategy is developed where two microwell platforms are used to increase the loading efficiency of the microwells. Cells are first loaded onto a smaller microwell array where almost all wells are loaded with single cells due to size exclusion (each well size~cell diameter). Once saturated, the smaller microwell is aligned with the larger microwell array and cells are transferred to larger wells. This enables high-efficiency loading of larger microwell arrays, which offers a larger area for mRNA capture, for example.

Example 5. Deterministic Cell Trapping and Transfer Approach for High-Throughput Interfacing of ~30,000 Single Cells to High-Density Barcode Array While the random cell loading such as the one described in Example enables a straightforward operation, a more deterministic approach helps improve throughputs by ensuring that almost all barcoded patches are interfaced with a single cell. For this purpose, a cell trapping and transfer method to reliable placing single cells into microwell/chambers for molecular analysis is demonstrated (FIG. 9), which involves two set of microwell devices, one where the width of microwells is approximately equal to the diameter of cells of interest and another with larger-sized microwells. Once the small microwell PDMS chip is saturated with cells, the cell enter the microwells capturing only one cell per well due to size exclusion. Afterwards, extra cells are washed out and this small microwell with cells trapped is placed against the array of larger-sized microchambers where cells are transferred to the larger chambers by gravity and pushing the back of the small microwell silicone chip. This process can be optimized and repeated such that nearly all microwells (>95%) are occupied by single cells. This process thereby enables improved throughputs while at the same time using larger wells (to provide an increased surface area coated with barcoded oligos for more efficient mRNA capture). Approximately 30,000 single cell microchambers per chip can be achieved, and this performance is well above the requirement and ensures ultra-high-throughput single-cell transcriptome analysis.

Example 6. Cell Lysis and mRNA Capture from Single Cells

Figure 10:
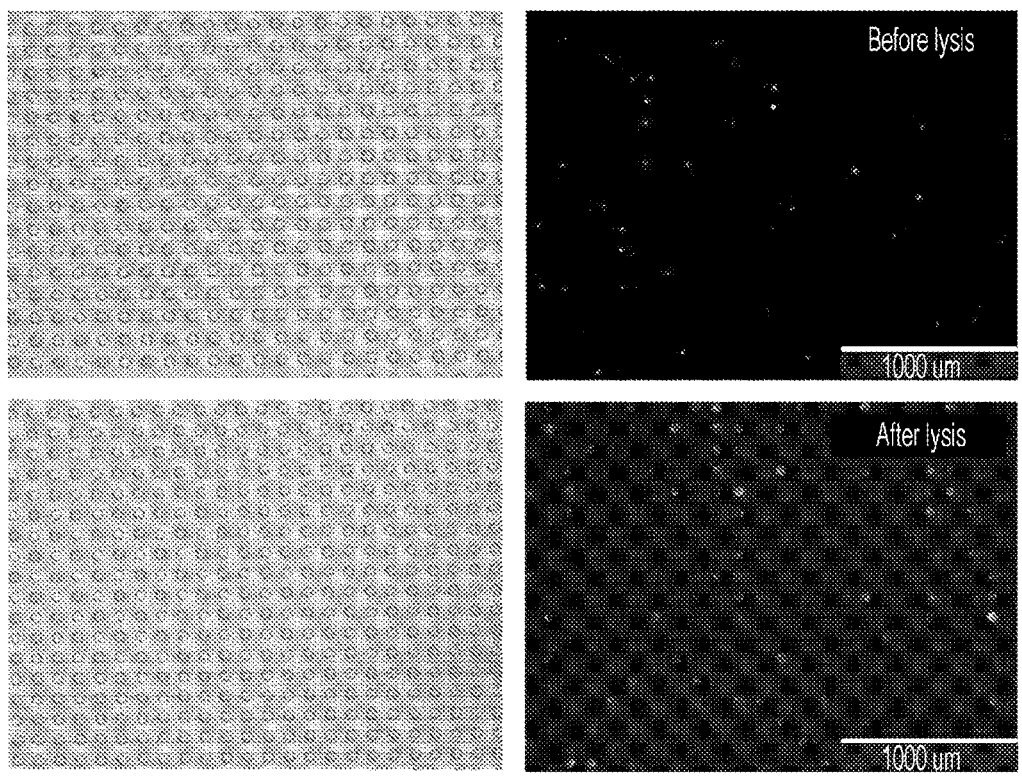
FIG. 10: Example of cell lysis in microwell arrays using freeze-thaw method. The top images depict a field of view of microwells that are loaded with single cells labeled with green fluorescent stain (cells are not visible in bright field images). The bottom two images show the cells after two freeze-thaw cycles. Cell lysis is apparent by the diffusion of fluorescent stain into the whole volume of individual wells. Sealing maintains cell lysate within each well, preventing leakage. Other lysis methods including but not limited to detergent-based, thermal-coating or spay-coating of lysis buffer may be used.

Once the cells are captured in microwells and overlaid with the high-density barcode array (or sealed with a second glass slide on top in case of devices described in Example 4), they can be lysed using a few cycles of freezing and thawing (FIG. 10). During the freeze-thaw cycles, cell membranes are broken due to ice-formation and intracellular contents are released into microwells. Similarly, more selective cell lysis methods can also be used to controllably lyse the cytoplasm only (or both cytoplasm and nucleus) by controlling the concentration of detergents used in the lysis solution. Alternatively, w the dried lysis buffer may be spray coated onto the high-density barcode array (or another sealing glass slide) to initiate lysis once the microwells are sealed. Upon lysis, the devices are incubated for 1 h to capture the mRNA onto the barcoded oligos terminated with poly(dT) sequences.

Example 7. Library Preparation, Sequencing, and Bioinformatics

Figure 11:
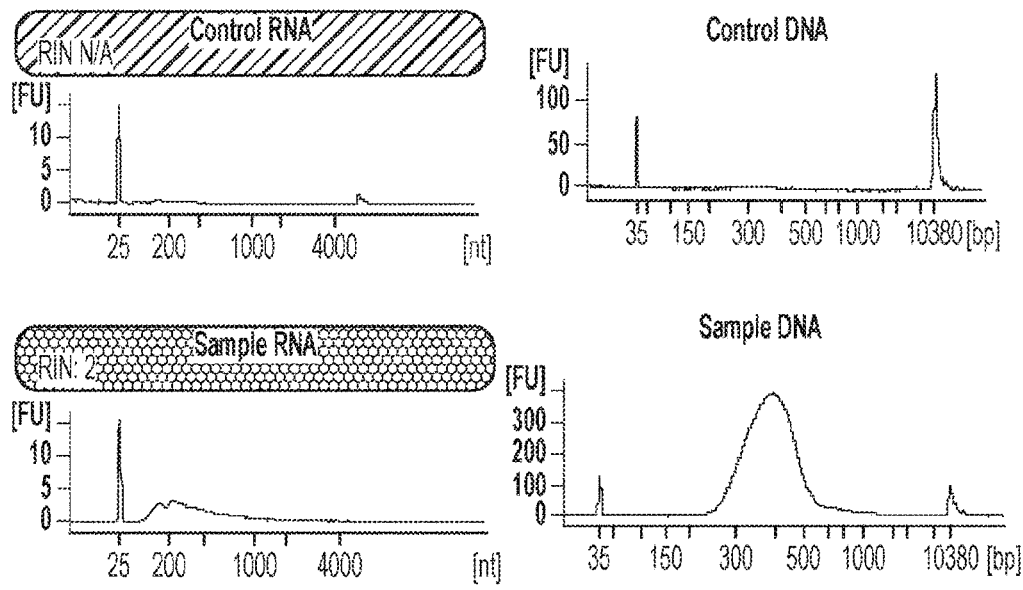
FIG. 11: Quality check of library preparation procedures applied in the system described. Bulk cell lysate from ~500,000 cells is applied to high-density barcode array. As a control, RNAse free water was applied onto the high-density barcode array. Libraries were prepared following the CelSeq2 protocol High sensitivity bio analyzer. Results showed successful library preparations from the lysate-applied barcode array, where sample RNA and DNA showed expected curves with average sizes at 300 bp and 400 bp. The control barcode array yielded no detectable RNA or DNA.

Library preparation follows the Cel-seq2 protocol. After the mRNA capture, the mRNA is reverse-transcribed followed by second strand synthesis. The generated cDNA is then in vitro transcribed to amplify the material captured. Amplified RNA (aRNA) is reverse transcribed and sequencing adapters are added through PCR amplification to finalize the libraries. The quality of library preparation is checked using a high sensitivity bioanalyzer (FIG. 11). The sequencing is done using the Illumina sequencers and data is analyzed using both available and custom bioinformatics tools.

Example 8. Multi-Omic Measurements

Figure 12:
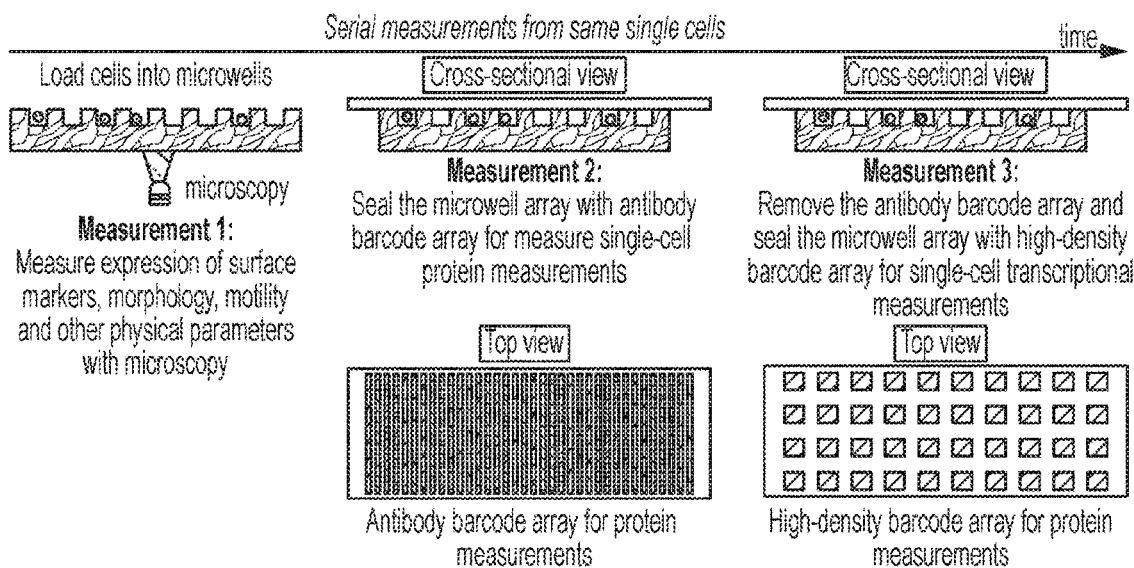
FIG. 12: Example of polyomics measurements from same single cells via serial measurements. After cell loading, cells are imaged through various microscopy imaging techniques to record surface marker expression, morphology, motility and other relevant physical phenotypes. The wells are then sealed with an antibody barcode array (see International Publication No. WO 2014/031997, published Feb. 27, 2014, incorporated herein by reference) to measure secretion of ~45 proteins. Next, the antibody barcode array is removed and replaced by a high-density barcode array for transcriptomic measurements. The data from same single cells are then integrated and analyzed together using custom software.

The approach described here affords the capability to obtain polyomic measurements from same single cells. This can be achieved either through serial measurements where, for example, first up to 45 secreted proteins can be measured by interfacing the microwells with an antibody barcode followed by transcriptomic measurement by interfacing the same cells with high-density barcode array for mRNA capture (FIG. 12). It can also be achieved through parallel measurements by interfacing the microwell array with two glass slides, one is the high-density barcode array for transcriptomic measurements and the other is a second glass slide for protein, microRNA or epigenetic measurements (FIGS. 13 and 14). In addition, this approach allows for imaging of individual cells trapped in each microchamber and thus permits simultaneous measurement of live cell behaviors (size, morphology, migration, etc.) in conjunction with gene expression and proteomic profiling, all on the same single cells.

Example 9. Barcode and Sequence Design

Row and column barcodes are separated by a constant sequence. Row barcodes are designed to be between 8 and 11 bases, such that the constant region will shift a base with each longer row barcode and this will prevent any sequencing issues related to sequencing problems with constant regions.

Individual sequences containing row barcodes and column barcodes

| Name | Sequence | Barcodes | Barcode complement |
|---|---|---|---|
| Row_V1_ 8 bp | CGATTGAGCCGGTTTTTTTAAGCAGTGGTATC AACGCAGAGTACAGTACATCGAGTGATTGCT TGTGACG (SEQ ID NO: 1) | AGTACATC | GATGTACT |
| Row_V1_ 9 bp | CGATTGAGCCGGTTTTTTTAAGCAGTGGTATC AACGCAGAGTACCACGTCAGTGAGTGATTGC TTGTGACG (SEQ ID NO: 2) | CACGTCAGT | ACTGACGTG |
| Row_V1_ 10 bp | CGATTGAGCCGGTTTTTTTAAGCAGTGGTATC AACGCAGAGTACGTACGTGAGCGAGTGATTG CTTGTGACG (SEQ ID NO: 3) | GTACGTGAGC (SEQ ID NO: 9) | GCTCACGTAC (SEQ ID NO: 11) |
| Row_V1_ 11 bp | CGATTGAGCCGGTTTTTTTAAGCAGTGGTATC AACGCAGAGTACTCGTAGCTCGTGAGTGATT GCTTGTGACG (SEQ ID NO: 4) | TCGTAGCTCGT (SEQ ID NO: 10) | ACGAGCTACGA (SEQ ID NO: 12) |
| Column_ V1_1 | AAAAAAAAAAAAAAAAAAAAAAAAAAAAAA NNNNNNNNNTACGAGCTGTCATCAGCGTCACA AGCAATCACTC (SEQ ID NO: 5) | AGCTCGTA | TACGAGCT |
| Column_ V1_2 | AAAAAAAAAAAAAAAAAAAAAAAAAAAAAA NNNNNNNNNCGACTCAGGTCATCAGCGTCACA AGCAATCACTC (SEQ ID NO: 6) | CTGAGTCG | CGACTCAG |
| Column_ V1_3 | AAAAAAAAAAAAAAAAAAAAAAAAAAAAAA NNNNNNNNNATGTGAGCGTCATCAGCGTCACA AGCAATCACTC (SEQ ID NO: 7) | GCTCACAT | ATGTGAGC |

| Name | Sequence | Barcodes | Barcode complement |
|---|---|---|---|
| Column_V1_4 | AAAAAAAAAAAAAAAAAAAAAAAAAAAAAA NNNNNNNNGCGACATAGTCATCAGCGTCACA AGCAATCACTC (SEQ ID NO: 8) | TATGTCGC | GCGACATA |

Fully extended sequences with both row and column barcode sequences

| Full 1 | CGATTGAGCCGGTTTTTTTAAGCAGTGGTATCAACGCAGA GTACAGTACATCGAGTGATTGCTTGTGACGCTGATGACAG CTCGTANNNNNNNNNTTTTTTTTTTTTTTTTTTTTTTTTT TTTT (SEQ ID NO: 13) |
|---|---|
| Full 2 | CGATTGAGCCGGTTTTTTTAAGCAGTGGTATCAACGCAGA GTACCACGTCAGTGAGTGATTGCTTGTGACGCTGATGACC TGAGTCGNNNNNNNNNTTTTTTTTTTTTTTTTTTTTTTTT TTTTT (SEQ ID NO: 14) |
| Full 3 | CGATTGAGCCGGTTTTTTTAAGCAGTGGTATCAACGCAGA GTACGTACGTGAGCGAGTGATTGCTTGTGACGCTGATGAC GCTCACATNNNNNNNNNTTTTTTTTTTTTTTTTTTTTTTT TTTTTT (SEQ ID NO: 15) |
| Full 4 | CGATTGAGCCGGTTTTTTTAAGCAGTGGTATCAACGCAGA GTACTCGTAGCTCGTGAGTGATTGCTTGTGACGCTGATGA CTATGTCGCNNNNNNNNNTTTTTTTTTTTTTTTTTTTTTT TTTTTTT (SEQ ID NO: 16) |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A polyomic multiplexing device, comprising:
a substrate comprising X rows intersecting (i) Y columns to form X*Y patches, and (ii) $Z_{n+1}$ columns to form X*Z patches, wherein each of the X*Y patches comprises a unique nucleic acid barcode that is immobilized to the substrate and comprises a polyT sequence, wherein:
each of the rows comprises a different subset of barcoded nucleic acid strands of a first set of nucleic acid strands, and each of the Y columns comprises a different subset of barcoded nucleic acid strands of a second set of nucleic acid strands,
the nucleic acid strands of the first set are bound to nucleic acid strands of the second set to form the unique nucleic acid barcode at each of the X*Y patches,
the unique nucleic acid barcode comprises, in the 5' to 3' direction, a barcode sequence of the first set, a barcode sequence of the second set, and a polyT sequence,
each of the X*Z patches comprises an antibody immobilized to the substrate, and
n is zero or greater;
and
an array of microwells coupled to the substrate, wherein each microwell comprises one of the unique molecular barcodes immobilized the substrate and at least one of the antibodies immobilized to the substrate.

2. The polyomic multiplexing device of claim 1, wherein X is at least 10.

3. The polyomic multiplexing device of claim 2, wherein X is 10 to 20000.

4. The polyomic multiplexing device of claim 1, wherein Y is at least 10.

5. The polyomic multiplexing device of claim 4, wherein Y is 10 to 20000.

6. The polyomic multiplexing device of claim 1, wherein n is at least 1, and each of the $Z_{n+1}$ columns comprises a different antibody.

7. The polyomic multiplexing device of claim 6, wherein n is at least 2, and each of the $Z_{n+1}$ columns comprises a different antibody.

8. The polyomic multiplexing device of claim 1, wherein the microwell array comprises at least 20 microwells.

9. The polyomic multiplexing device of claim 1, wherein the nucleic acid strands of the first set of nucleic acid strands comprise, in the 5' to 3' direction: a promoter sequence, a sequencing adaptor sequence, a first barcode sequence and a first anchor sequence.

10. The polyomic multiplexing device of claim 1, wherein the nucleic acid strands of the second set of nucleic acid strands comprise, in the 5' to 3' direction: a polyT sequence, a unique molecular identifier sequence, a second barcode sequence and a second anchor sequence, wherein the second anchor sequence is complementary to the first anchor sequence.

11. The polyomic multiplexing device of claim 1, wherein the unique nucleic acid barcode comprises, in the 5' to 3' direction: a promoter sequence, a sequencing adaptor sequence, a first barcode sequence, a second barcode sequence, a unique molecular identifier, and a polyT sequence.

12. The polyomic multiplexing device of claim 1, wherein the substrate comprises glass, silicon or silica.

13. The polyomic multiplexing device of claim 1, wherein the substrate is coated with poly-1-lysine.

14. The polyomic multiplexing device of claim 1, wherein each column and/or row has a width of 50-200 microns.

15. The polyomic multiplexing device of claim 1, wherein each patch has an area of 400-40,000 $\mu m^2$.

16. The polyomic multiplexing device of claim 1, wherein patches within a single row and/or within a single column are separated from each other by 20-200 microns.

17. The polyomic multiplexing device of claim 1, wherein patches between adjacent rows and/or between adjacent columns are separated from each other by 20-200 microns.

* * * * *

UNITED STATES PATENT AND TRADEMARK OFFICE
CERTIFICATE OF CORRECTION

| | |
|---|---|
| PATENT NO. | : 11,753,743 B2 |
| APPLICATION NO. | : 16/485326 |
| DATED | : September 12, 2023 |
| INVENTOR(S) | : Rong Fan et al. |

It is certified that error appears in the above-identified patent and that said Letters Patent is hereby corrected as shown below:

On the Title Page

At item (72), the place of residence of inventor Burak Dura "Waltham, CO (US)" should be replaced with: --Lafayette, CO (US)--.

In the Claims

In Claim 13:
"the substrate is coated with poly-1-lysine."
Should read:
--the substrate is coated with poly-l-lysine.--.

Signed and Sealed this
Fourteenth Day of November, 2023

Katherine Kelly Vidal
*Director of the United States Patent and Trademark Office*